United States Patent [19]

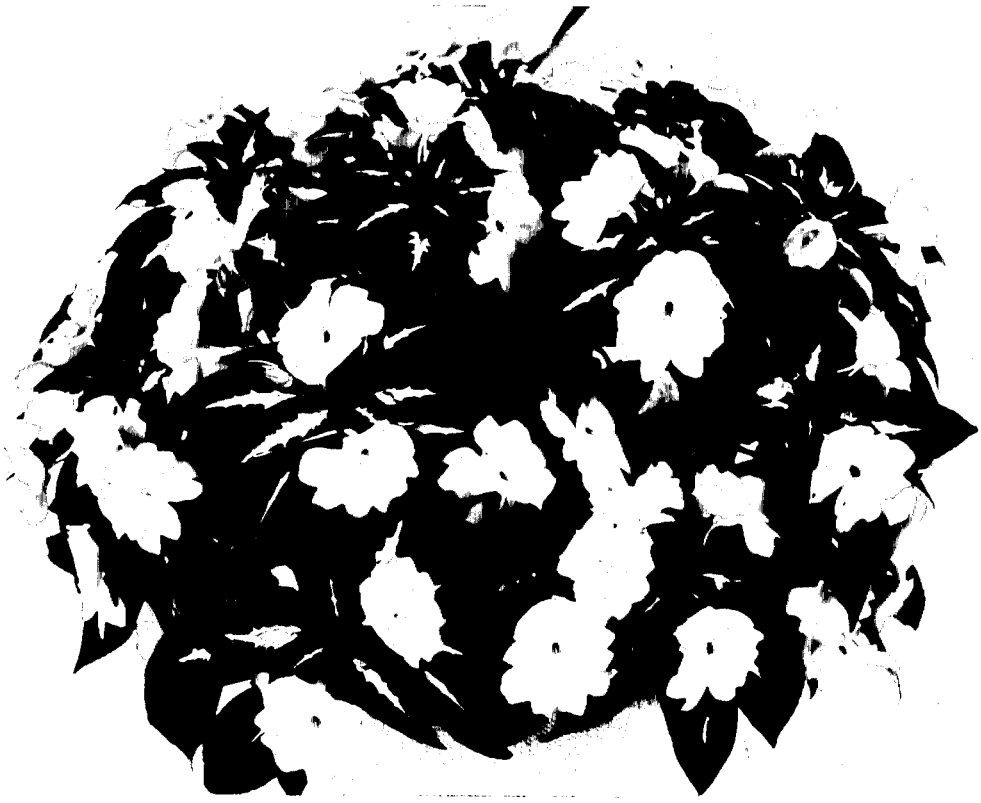

Mikkelsen

[11] Patent Number: Plant 5,804

[45] Date of Patent: Nov. 18, 1986

[54] IMPATIENS PLANT NAMED ZENITH

[75] Inventor: James C. Mikkelsen, Ashtabula, Ohio

[73] Assignee: Mikkelsens, Inc., Ashtabula, Ohio

[21] Appl. No.: 663,038

[22] Filed: Oct. 19, 1984

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

An Impatiens plant named Zenith, having deep orange, large flowers, vigorous, self-branching mounded growth habit making it useful for pot and border plant use; relatively large glossy green leaves with a distinct toothed midrib variegation, and by its adaptability to various environments of use.

1 Drawing Figure

The present invention relates to a new and distinctive cultivar of New Guinea Impatiens plant, botanically known as Impatiens, and referred to by the cultivar name Zenith.

Zenith was developed by me in Ashtabula, Ohio, through controlled breeding by crossing Mikkelsen Seedling No. 82-749-3 (seed parent)×Mikkelsen Seedling No. 82-795-3 (pollen parent). Asexual reproduction by terminal or stem cuttings taken by me in Ashtabula, Ohio, has shown that the unique features of this new Impatiens are stabilized and are reproduced true to type in successive propagations.

The following characteristics distinguish Zenith from both its parent varieties and other cultivated Impatiens of this type known and used in the floriculture industry:

1. It is a larger, more vigorous plant than Solared, disclosed in U.S. Plant Pat. No. 5,131, and Comet, disclosed in my pending application. It is similar in plant size to Sunset (unpatented) and Columbia, disclosed in U.S. Plant Pat. No. 5,126, but is more mounded than either.

2. The flower color of Zenith is deeper than Sunset and lighter than Eclipse, disclosed in U.S. Plant Pat. No. 4,689. The flower color is similar to Halo, U.S. Plant Pat. No. 4,725, but Zenith has a much larger flower and better flower shape.

3. Flowers have excellent keeping qualities, and the flowers cover the mound from the ground to the top of the plant. It is similar in flowering habit to Sunset but the flowers are larger.

4. It is self-branching and a vigorous grower, with its mounded growth habit making it ideal for pots, hanging baskets and bedding.

5. Leaf is similar to Sunset with a toothed variegation pattern similar to Sunset, but not as pronounced. Leaves are larger than Comet and Solared, and have a glossy surface.

6. Plant and flowers have low temperature tolerance when gradually acclimated to the outdoor temperature, as was demonstrated by plants withstanding 2.2° C. in May.

7. Flowering is slower to start than Comet, Pulsar and Quasar (the latter two cultivars being disclosed in pending applications), but once flowering starts the large flowers cover the plant and flowering is continuous throughout season.

8. Its shape and flower size make Zenith a good cultivar for further hybridizing for pot plants and border plants.

The accompanying colored photograph taken in March 1984 illustrates the overall appearance in perspective view of Zenith, showing the colors as true as it is reasonably possible to obtain in a colored reproduction of this type.

The following is a detailed description of my new Impatiens cultivar based on plants produced under commercial practices in Ashtabula, Ohio, grown in 5.5" green plastic pots during the winter of 1983–1984, and describes colors under reduced sunlight, and early, floriferous flowering. Color references are made to The Royal Horticultural Society Colour Chart except where general terms of ordinary dictionary significance are used.

Parentage: Mikkelsen Seedling No. 82-749-3×Mikkelsen Seedling No. 82-795-3.

Propagation:

(A) *Type cutting.*—Stem 15 to 20 mm long will develop 4 to 5 cm long in 18 to 21 days.

(B) *Time to root.*—8 to 10 days at 23° C. summer, and 10 to 12 days at 20° C. winter.

(C) *Rooting habit.*—Mass of fiberous roots from the stem.

Plant description:

(A) *Form.*—Symmetrically mounded, compact, self-branching, green stemmed flowering herb.

(B) *Habit of growth.*—Vigorous, self-branching, with continuous flowering.

(C) *Foliage description.*—Broad, glossy green leaves with toothed variegation at the midrib. (1) Size: 6.5 to 7.5 cm long×2.0 to 2.5 cm wide. (2)Shape: Ovate with acuminate apex with acute base. (3) Texture: Rugose upper side, glabrous under side. (4) Margin: Serrated, finely ciliated. (5) Color: Young foliage, top side 146A to 147A, under side 146C. Mature foliage, top side 133A, under side 148B. (6) Venation: Pinnate.

Flowering description:

(A) *Flowering habits.*—Flowers continuously from leaf whorl in progressive, orderly manner, taking 5 to 7 days from large bud to bloom; flowers last 2 to 3 weeks.

(B) *Natural flowering season.*—Indeterminant and continuous. Quantity of flowers increase with increasing levels of light intensity and duration.

(C) *Flower buds.*—Ellipsoidal, flowers perfect, reddish orange spur 4.0 to 4.5 cm long with throat behind ovary and originating from the major sepal.

(D) *Flowers borne.*—From individual 3 cm pedicels from a whorl of five to six leaves, flowering progressively around the whorl as leaves and buds develop, and remaining just on top of the leaf canopy.

(E) *Quantity of flowers.*—Quite floriferous; flower development is continuous so that tight buds to mature blooms are visible at the same time.

(F) *Petals.*—(1) Shape: Heart shaped, top dominant, four others overlapping and symmetrical. (2) Color: Top side in winter when opening, 40A, fading to 33A, under side, 41B, fading to 41C. (3) Number of petals: Five (5) in number. (4) Size of flowers: 7.0 cm to 8.0 cm in diameter.

(G) *Reproductive organs.*—(1) Stamens: Five (5) in number. (a) Anther shape: Hooded, red orange 43C. (b) Pollen color: Cream. (2) Pistils: (a) Stigma shape: Five (5) in number, segmented column-shaped; white in color. (b) Style color: Clear. (c) Ovaries: five (5) in number, celled, size 6 mm until fertilized, green in color.

Disease resistance: No significant disease or insect problems have been seen to date.

Summary of important characteristics of new cultivar: (1) Large, very symmetrical flowers. (2) Compact, mounded and vigorous growth habit. (3) Variegation pattern of leaves.

I claim:

1. A new and distinct cultivar of New Guinea Impatiens plant named Zenith, as described and illustrated, and particularly characterized by its deep orange, large flowers, vigorous, self-branching mounded growth habit making it useful for pot and border plant use; relatively large glossy green leaves with a distinct toothed midrib variegation, and by its adaptability to various environments of use.

* * * * *